United States Patent
Hare (10) Patent No.: US 6,552,104 B1
(45) Date of Patent: *Apr. 22, 2003

(54) METHOD OF MAKING HYDROPHILIC NON-SWEATING POLYMERIZABLE DENTAL IMPRESSION MATERIAL

(75) Inventor: Robert V. Hare, Georgetown, DE (US)

(73) Assignee: Dentsply Research & Development Corp.

( * ) Notice: Subject to any disclaimer, the term of this patent is extended or adjusted under 35 U.S.C. 154(b) by 31 days.

This patent is subject to a terminal disclaimer.

(21) Appl. No.: 09/818,270

(22) Filed: Mar. 27, 2001

Related U.S. Application Data (63) Continuation of application No. 09/428,961, filed on Nov. 4, 1999, now abandoned, which is a continuation of application No. 09/235,535, filed on Jan. 22, 1999, now abandoned, which is a continuation-in-part of application No. 09/088,183, filed on Jun. 1, 1998, now Pat. No. 5,955,513, which is a continuation-in-part of application No. 08/910,874, filed on Jul. 13, 1997, now Pat. No. 5,863,965, which is a continuation of application No. 08/612,630, filed on Mar. 6, 1996, which is a continuation of application No. 08/490,690, filed on Apr. 13, 1995, now Pat. No. 5,661,222.

(51) Int. Cl.$^7$ ................................................. A61K 6/10

(52) U.S. Cl. ........................... 523/109; 528/15; 528/31; 528/32; 528/39; 525/478; 106/35; 106/38.22; 264/16; 433/214; 524/493; 524/588

(58) Field of Search ............................ 523/109; 106/35; 106/38.22; 264/16; 433/214; 524/493, 588; 525/478; 528/15, 31, 32, 39

(56) References Cited

U.S. PATENT DOCUMENTS

| | | | |
|---|---|---|---|
| 4,222,983 A | 9/1980 | August et al. ............... 264/220 |
| 4,340,709 A | 7/1982 | Jeram et al. ................... 528/15 |
| 4,359,565 A | 11/1982 | Puppe et al. ................... 528/15 |
| 4,568,707 A | 2/1986 | Voigt et al. .................. 523/109 |
| 4,600,731 A | 7/1986 | Louis et al. .................. 523/109 |
| 4,614,758 A | * 9/1986 | Schwabe et al. ............. 524/487 |
| 4,657,959 A | 4/1987 | Bryan et al. ................. 524/266 |
| 4,752,633 A | * 6/1988 | Aasen et al. ................. 524/266 |
| 4,965,295 A | 10/1990 | Schwabe et al. ............. 523/109 |
| 5,064,891 A | 11/1991 | Fujikil et al. ................ 524/264 |
| 5,066,714 A | 11/1991 | Inoue et al. .................. 524/731 |
| 5,367,001 A | 11/1994 | Itoh et al. .................... 523/109 |
| 5,403,885 A | 4/1995 | Voigt et al. .................. 524/731 |
| 5,484,871 A | 1/1996 | Stepp ........................... 528/31 |
| 5,555,584 A | 9/1996 | Moore, III et al. ............ 12/142 |
| 5,569,691 A | 10/1996 | Guggenberger et al. .... 524/261 |
| 5,580,921 A | * 12/1996 | Stepp et al. ................. 524/731 |
| 5,584,886 A | 12/1996 | Lai ............................. 623/11 |
| 5,659,001 A | 8/1997 | De la Croi Haimana et al. ............................. 528/17 |
| 5,661,222 A | 8/1997 | Hare ........................... 525/478 |
| 5,750,589 A | * 5/1998 | Zech et al. .................. 523/109 |
| 5,830,951 A | * 11/1998 | Fiedler ........................ 525/478 |
| 5,849,812 A | * 12/1998 | Zech et al. .................. 523/107 |
| 5,852,068 A | * 12/1998 | Jada ........................... 523/109 |
| 5,863,965 A | 1/1999 | Hare ........................... 523/109 |
| 5,907,002 A | * 5/1999 | Kamohara et al. ........... 523/109 |
| 5,955,513 A | * 9/1999 | Hare ........................... 523/109 |
| 6,013,711 A | * 1/2000 | Lewis et al. ................. 524/265 |
| 6,121,362 A | * 9/2000 | Wanek et al. ............... 524/448 |
| 6,201,038 B1 | * 3/2001 | Waller et al. ................ 523/100 |

FOREIGN PATENT DOCUMENTS

| | | |
|---|---|---|
| DE | 41 29 613 | 3/1993 |
| EP | 0 286 347 | 5/1988 |
| EP | 0 480 238 | 4/1992 |
| EP | 0 522 341 | 1/1993 |
| EP | 0 602 128 B1 | 6/1994 |
| EP | 0 614 655 | 9/1994 |
| GB | 2 292 153 | 2/1996 |
| WO | 93/04659 | 3/1993 |
| WO | 93/17654 | 9/1993 |
| WO | 96/32088 | 10/1996 |

OTHER PUBLICATIONS

Revised American Dental Association Specification No. 19 for Non–Aqueous, Elastomeric Dental Impression Materials; Reports of councils and Bureaus; JADA, vol. 94, Apr. 1977, pp. 733–741.

Addendum to American National Standards Institute/American Dental Association specification No. 19* for dental elastomeric impression material; JADA, vol. 105, Oct. 1982.

* cited by examiner

Primary Examiner—Margaret G. Moore
(74) Attorney, Agent, or Firm—Dale R. Lovercheck; James B. Bieber (57) ABSTRACT

Improved very high viscosity (putty) two component polymerizable polyorganosiloxane composition for use in making non-sweating, low liquid mass loss dental impressions, having improved tear strength, handling and wettability. Improved tear strength results from inclusion of a quadrifunctional polysiloxane having a vinyl content of 0.16 to 0.24 m-mole/g. Working time is maintained by including sufficient amounts of a retarder composition that delays onset of the vinyl polymerization. Handling is improved by the addition of a very high viscosity linear vinyl terminated polydimethylsiloxane which reduces tackiness and improves the shelf stability. Wettability is improved by including a surfactant resulting in a surface contact angle with water at three minutes of less than 50°. The surfactant chosen has an HUB of 8–11, such that the wetting contact angle is achieved within less than two minutes and remains wetting throughout the working time of the impression taking, substantially improving the impression making process.

14 Claims, 2 Drawing Sheets

Fig. 1

Fig. 2

METHOD OF MAKING HYDROPHILIC NON-SWEATING POLYMERIZABLE DENTAL IMPRESSION MATERIAL

This application is a continuation of application Ser. No. 09/428,961, filed Nov. 4, 1999 (status: abandoned), which is a continuation of application Ser. No. 09/235,535, filed Jan. 22, 1999, (now abandoned), which is a Continuation-in-Part of U.S. patent application Ser. No. 09/088,183 filed Jun. 1, 1998, now U.S. Pat. No. 5,955,513 which is Continuation-in-Part of U.S. patent application Ser. No. 08/910,874 filed Jul. 13, 1997 (Case 1833-1CIP FWC) now U.S. Pat. No. 5,863,965 which is a Continuation of U.S. patent application Ser. No. 08/612,630 filed Mar. 6, 1996 which is a Continuation of U.S. patent application Ser. No. 08/490,690 filed Apr. 13, 1995, now U.S. Pat. No. 5,661,222.

BACKGROUND OF THE INVENTION

This invention is directed to improvements in room temperature polymerizable polyorganosiloxanes having very high viscosity (putty) and good dimensional stability upon curing or hardening. More particularly, this invention is directed to improvements in compositions that are generally of the type comprising two components, one component comprising organopolysiloxanes having vinyl groups, capable of undergoing addition reactions with organopolysiloxanes having silicone-bonded hydrogen atoms. The second component comprises a catalyst capable of promoting the addition of hydrogen atoms bonded to silicone atoms across the vinyl groups.

A major field for the use of certain of these room temperature curable polyorganosiloxane compositions is dentistry. Such materials are typically employed as impression materials for securing an analog representation of oral bard and soft tissue to support subsequent elaboration of crowns, bridges, dentures, an other oral prostheses. For dental use, extraordinary fidelity of structural reproduction is required in order to ensure good fidelity of oral prosthetic fit and the like. In this regard, changes in the dimensions of the impression material during curing are to be avoided. Moreover, the surface of the reproductions or oral prosthetics and the like must be exceptionally free from irregularities, blemishes, pits, and other imperfections. This is so because castings and prostheses derived from such impressions must have good surface qualities and be free from pits and irregularities in order to have proper fit, to achieve good adhesion, and to avoid irritation of sensitive mouth structures. These polyorganosiloxanes will also be useful in other fields where detailed reproductions are important such as in the science of metrology, laboratory processing of SEM and even jewelry fabrication and the like.

In employing polyorganosiloxanes as dental impression materials, a number of difficulties have arisen. First of all, tear strength tends to be low. It is necessary, in effectively taking an impression, to be able to easily remove the impression, from the dentition without tearing, particularly at thin marginal areas, to preserve fine detail. In the past, fillers of various types have been added to improve tear strength. Such additions may result in some improvement, on the order of about 10%, but such improvements have proved inadequate.

Paradiso in WO 93/17654 describes improving tear strength by incorporating multi-functional, including quadri-functional, polysiloxane components into the impression material, to add increased cross-linking to the resulting cured impression material matrix, particularly along the length of the linear vinyl end-stopped polysiloxane principal component. The Paradiso composition comprises SiOH groups capped off with $Me_3Si$ units that form pendants from the molecule. These pendants provide only mechanical or physical interlinking between the linear polysiloxane chains. This solution is deficient, being non-chemical and low in cross-linking density.

Voigt et al in EP 0 522 341 A1 describes very short processing times of 35–45 seconds for forming dentition bite registration devices, utilizing a "QM" resin as a means of speeding and increasing cross-linking. These resins comprise as Q, the quadri-functional $SiO_{4/2}$ and as M, building blocks such as monofunctional units $R_3SiO_{1/2}$ wherein R is vinyl, methyl, ethyl or phenyl, or similar tri or bi-functional units. Voigt also notes that an elastomer with small elastic deformation having a higher tenacity and hardness results. However, hydrophobic poor wetting, such material lacks flexibility, having a low strain value, and is unsuitable for impression taking. The increased cross-linking rate of the QM resin also results in very limited processing times that are unsatisfactory.

The other major, well-known difficulties with polyorganosiloxane impression materials are caused by its inherent hydrophobic character. Such characteristics make reproduction of hard and soft oral tissue difficult since the oral cavity environment is wet and often contaminated with saliva or blood. The hydrophobicity of the impression material can result in loss of surface detail often at critical surfaces of the dentition.

A number of improvements of polyorganosiloxane impression materials focus upon adding a surfactant component to the dental impression material in order to reduce the hydrophobic nature of the polysiloxanes and make the composition more hydrophilic. Thus, Bryan et al in U.S. Pat. No. 4,657,959 describes adding an ethoxylated nonionic surface active agent containing siloxane or perfluoroalkyl solubilizing groups to achieve a three minute water contact angle below about 65°. While surfactants including hydrocarbyl groups, for rendering the surfactant soluble or dispersible in silicone prepolymer, are mentioned, including ethyleneoxy groups, the results achieved appeared to be less than optimal. Wetting but low tear strength.

In sum, polyorganosiloxane impression materials still need improvement in tear strength and wettability in order to provide improved use of these compositions for taking impressions of oral hard and soft tissues such that adequate working time, tear strength and wettability are provided. Also, sweating occurs as a result of the plasticizer that is in the composition migrating to the surface of the impression forming oily droplets of liquid. Sweating has been reported to cause melting of polystyrene impression trays and loss of impression detail.

Sweating as used herein refers to droplet formation of plasticizer formed on the outer surface of cured elastermeric impression material at 23° C. within 24 hours of curing the cured material.

Non-sweating as used herein refers to elastomeric impression material which does not form visible droplets (and/or a film) of plasticizer on the outer surface- thereof at 23° C. within 24 hours of curing the impression material.

Low liquid mass loss as used herein refers to elastomeric impression material which has less than 0.05 percent mass loss after 12 days at 23° C. from the start of curing the impression material. A specimen is made of the putty using ADA 19 detail reproduction mold. The specimen is placed on top of an absorbent paper towel in a labeled crystallization dish and covered with a watch glass. 12 days after mixing the putty, the surface of the putty is observed, a record of the readability of the detail reproduction is made. The specimen is gently touched (blotted) with the paper towel to absorb any "sweat" or oil from the surface. Then the specimen reweighed and the weight recorded. The results for the impression material of Example 1 and some commercially available dental impression materials are shown in the following Table I.

TABLE I

| Material | EXAMPLE 1 | REPROSIL | EXAFLEX | EXPRESS | EXTRUDE | PRESIDENT |
|---|---|---|---|---|---|---|
| Initial detail readability | 20 Micron | 20 Micron | 75 Micron | 75 Micron | 75 Micron | 50 Micron |
| Initial weight (+/−0.00001 Grams) | 4.09034 | 3.59762 | 5.00262 | 5.18539 | 4.28017 | 4.15028 |
| Final detail readability | 20 Micron | 20 Micron | 75 Micron | 75 Micron | failed 75 | 50 Micron |
| Final weight (+/−0.00001 Grams) | 4.08984 | 3.58888 | 4.99765 | 5.18025 | 4.27401 | 4.14442 |
| Difference between initial and final weights | −0.00050 | −0.00874 | −0.00497 | −0.00514 | −0.00616 | −0.00586 |
| % Mass loss | −0.01222 | −0.24294 | −0.09935 | −0.09912 | −0.14392 | −0.1412 |

Non-sweating preferably refers to elastomeric impression material which after storage at 23° C. for 24 hours has less than 10% by weight of the placticizer in the starting material separated from the stored impression material to form droplets (or a film) on the outer surface of the stored material. More preferably, there is less than 5% by weight of placticizer separated from material in accordance with the invention and most preferably, there is less than 1% by weight of placticizer separation from material in accordance with the invention.

Separation stable composition as used herein refers to a composition which is a single homogenous material after three weeks of storage in stationary position at 23° C., and thus has not separated into two or more materials, so that such separation is visibly apparent. The lower density liquids do not migrate to the upper surface of a separation stable composition.

Consistency as used herein refers to consistency as measured by ADA specification number 19 revised Oct. 4, 1976 and is measured in mm.

Putty material in accordance with the invention is useful for making dentures, crowns, inlays and onlays and other prosthetics. The dentist takes an impression of the patient's mouth by first applying a low viscosity material which is commonly dispensed from a syringe and then applying putty material in accordance with the invention over the low viscosity material. The putty material forces the low viscosity material into the minute details of the patient's mouth for which an impression is being taken. The putty material hardens within about five minutes and then is readily removable by the dentist. The low viscosity material also hardens within about five minutes. Typically the low viscosity material forms a thin partial coating and the putty material forms a comprehensive layer surrounding a dentition for which an impression is being taken. Beneficially, the putty material in accordance with the invention is hydrophilic and captures minute details of the dentition.

SUMMARY OF THE INVENTION

A very high viscosity putty polyvinylsiloxane impression material useful to record hard and soft tissues in the mouth. The new impression material is a two component, hydrophilic non-sweating polymerizable organosiloxane separation stable material. The two component polymerizable organosiloxane composition, one component including a catalyst for polymerization, is for making a dental impression and comprises:

(a) a QM resin, containing vinyl groups;

(b) a linear vinyl terminated polydimethyl-siloxane fluid, forming with said QM resin a dispersion having a vinyl content of about 0.16 to 0.24 m-mole/g;

(c) a very high viscosity linear vinyl terminated polydimethylsiloxane having a molecular weight of 400,000–500,000, vinyl content 0.03 mmole/g;

(d) an organohydrogen polysiloxane for cross-linking said vinyl groups;

(e) an organoplatinum catalyst complex for accelerating polymerization of said components;

(f) an emulsifying plasticizer;

Placticize is normally an oily liquid. Placticizer typically is a low molecular weight nonpolymerizable compound, for example having a gram molecular weight less than 2000 and a viscosity less than 200 CPS.

(g) a retarder component in sufficient amount for temporarily delaying the onset of said polymerization;

(h) a filler; and (i) a surfactant that imparts wettability to said composition, wherein said composition surface contact angle with water is less than 50° after three minutes.

In accordance with a preferred embodiment of the invention, the placticizer is a emulsified by the surfactant. The mixture of placticizer and surfactant form a homogeneous phase within the putty composition in accordance with the invention.

Preferably, the dispersion of (a) and (b) has a viscosity of about 45,000–60,000 cps. The dispersion of (a), (b) and (c) may comprise a plurality of dispersion components having desired viscosities and QM resin contents. Preferably the QM resin-containing dispersions comprise a dispersion component having a viscosity of about 45,000–60,000 cps, the QM resin comprising about 20–25 weight % of the dispersion.

A preferred QM resin comprises a polyorganosiloxane comprising units of $SiO_{4/2}$ an units of $R^1R^2{}_2 SiO_{1/2}$ wherein $R^1$ is unsaturated, preferably vinyl and $R^2$ is alkyl, aryl, etc., such as methyl, ethyl, phenyl, etc. More preferably, the QM resin comprises the formula:

The very high Viscosity linear vinyl terminated polydimethylsiloxane which imparts longer shelf stability, higher tear strength, reduced tackiness and improved tactile handling properties is preferably 5–15 percent by weight and most preferably 9–11 percent by weight of the composition.

The retarder component of the composition is a low molecular weight, vinyl functional fluid that is a linear or cyclic polysiloxane in an amount of at least about 0.010 weight percent of said composition. Preferably, the retarder component comprises: a fluid 1,3-divinyl, dimethyldisiloxane, in an amount of about 0.05 to 0.15 weight percent of said composition.

The composition includes a plasticizer that is capable of being emulsified to prevent "sweating" or migrating to the surface of the polymerized impression. The plasticizer is used to reduce tackiness of the composition during mixing of the base and catalyst components which are mixed by hand kneading. Preferably the plasticizer is comprised of an alkylphthalate, preferably at about 4–5 percent by weight of the base and catalyst compositions. Most preferably, the alkylphthalate is octyl benzyl phthalate.

The filler component of the invention comprises about 35 to about 55 weight percent of said composition and preferably includes a filler mixture of about 40 to about 50 weight percent.

A key component of the composition of the invention is the surfactant for imparting wettability, preferably comprising an HLB of about 8–11 and a pH of about 6–8. A most preferred surfactant is a nonionic surfactant, nonylphenoxy poly(ethyleneoxy) ethanol having an HLB of about 10.8. This surfactant also serves to emulsify the plasticizer and prevents its separation and "sweating" from the compositions.

After polymerization, the compositions of the invention include a tear strength of 300–400 psi and a contact angle with water of less than 50° at three minutes.

DESCRIPTION OF THE PREFERRED EMBODIMENTS

The two component, polymerizable polysiloxane compositions of the instant invention comprises, in general: an organopolysiloxane having at least about two vinyl groups per molecule, further including, dispersed therein, a quadri-functional vinyl polysiloxane resin; an organohydrogenpolysiloxane having at least about two hydrogen atoms bonded to at least two silicone atoms per molecule; a catalyst for accelerating the addition of the silicone atoms bonded to the hydrogen atoms to the polysiloxane vinyl groups, including an emulsifying plasticizer; a filler; a low molecular weight retarder composition for delaying onset of polymerization; and an emulsifying surfactant that imparts wettability to said impression material.

The composition of the invention is divided into two components. A first component, which is conveniently referred to as "Base paste", contains the vinylorganopolysiloxane dispersion, the very high viscosity linear vinyl terminated polydimethylsiloxane, the organohydrogen polysiloxane, a portion of the filler, pigmented, the plasticizer, and the surfactant. The second component of this two part composition is referred to as a "catalyst paste", and comprises a second portion of the vinylorganopolysiloxanes, verb high viscosity linear vinyl terminated polydimethylsiloxane, together with the platinum catalyst for accelerating the addition reaction, the plasticizer, a scavenging agent for hydrogen released during polymerization additional quantities of filler and pigments A wide variety, of organopolysiloxanes having at least about two vinyl groups per molecule are known for inclusion in the dental polysiloxane compositions of the invention to form the dispersion including a quadri-functional vinyl polysiloxane. Each of these materials may be included in greater or lesser degree in accordance with the practice of the instant invention. Preferred for use herein are linear vinyl terminated polydivinylsiloxanes preferably a divinyl poly-dimethylsiloxane. Such polymers are sold having varying average molecular weights with concomitant variations in viscosity. It is preferred that these materials be selected to have a viscosity appropriate for the conditions to be experienced by the resulting silicone material.

The dispersions of interest have a viscosity range of 45,000–60,000 cps. In practice, it is convenient to employ a blend of the dispersing polymers having differing viscosities and physical properties to provide compositions having a desired thixotropicity and viscosity.

The dispersion of interest is preferably formed in the viscosity range of about 45,000–65,000 cps. While it is convenient to provide polysiloxane oligomers for this purpose having methyl substituents, other substituents may also be included in the compositions in accordance with this invention. Thus, alkyl, aryl, halogen, and other substituents may be included in greater or lesser degree as part of the vinyl polysiloxanes which are useful. Those of ordinary skill in the art will be able to determine which polysiloxane materials are preferred for any particular utility from the foregoing considerations.

The quadri-functional polysiloxanes, designated and known in the art as QM resins, provide improved tear strength to the polymerized impression composition, by increasing its resulting polymerized crosslink density. As is known, the QM resin is made up of: quadri-functional $SiO_{1/2}$ units; and M units, such as $R^1R^2{}_2SiO_{1/2}$ wherein $R^1$ is unsaturated, preferably vinyl and $R^2$ is alkyl, aryl or the like, such as methyl, ethyl or phenyl. In a preferred composition $R^1$ is vinyl and both $R^2$ are methyl. A most preferred composition is represented by the formula:

The QM resin provides a vinyl concentration in the dispersions with the vinyl-terminated polydivinylsiloxaznes of at least about 0.16 m-mole/g. Preferably the vinyl concentration is 0.16–0.24 m-mole/g. The amount of QM resin is preferably about 20–25% by weight of the dispersion. Such dispersions are sold by Bayer Silicones of Pittsburg, Pa. Other QM resin formulations may be used, including those that are "neat" or dispersed in carriers other than the preferred fluid polydivinylsiloxane.

The very high viscosity linear vinyl terminated polydimethylsiloxane which imparts improved shelf stability, tear strength and tackile handling properties is preferably 5–15 percent by weight and most preferred 9–1 percent by weighs of the composition. The molecular weight is 400,000–500,000 and vinyl content 0.02–0.04 m-mole/g.

A key element of the invention is a retarder component that delays onset of polymerization of the QM resin/dispersion such that sufficient working times to employ the composition are provided It functions, as it is consumed, to offset what would otherwise be a too rapid polymerization. The preferred retarder fluid in the preferred impression material of interest is 1,3 divinyldimethyldisiloxane at a sufficient concentration level to perform its retarding functions, which is in at least about 0.10 weight percent of the composition, preferably within a range of about 0.05 to 0.15 weight percent. This preferred amount is in contrast with the lower amounts of 0.0015–0.020 weight percent typically employed in PVS systems to stabilize compositions. Other suitable retarders are any low molecular weight, vinyl functional material that would be initially consumed in the polymerization, to delay hardening suitably and as desired, including linear and cyclic polysiloxanes.

The organohydrogen-polysiloxanes useful in the practice of the present inventions are well-known to those of ordinary skill in the art. It is required only that polysiloxanes having hydrogen atoms directly bonded to silicone atoms be employed, and that they have suitable viscosities and other physical properties. Substituents in the molecules such as alkyl (especially methyl), aryl, halogen, and others may be employed as well. It is necessary only that such substituents not interfere with the platinum-catalyzed addition reaction. It is preferred that molecules be employed having at least two silicone-bonded hydrogen atoms per molecule. Polymethylhydrogensiloxane is preferred, having a viscosity range of about 35–45 cps.

The catalysts which are useful for catalyzing the reaction of the silicone atoms (bonded to hydrogen atoms) to the vinyl groups of the vinyl polysiloxane molecules are preferably based upon platinum. In this regard, it is preferred to employ a platinum compound such as chloroplatinic acid, preferably in admixture or complex with one or more vinyl materials, especially vinyl polysiloxanes.. While such materials have been found to be preferred, other catalysts are also useful. Thus, platinum metal together with other noble metals including palladium, rhodium, and the like and their respective complexes and salts are also useful. In view of the toxicological acceptability of platinum, however, it is greatly to be preferred for dental use.

The compositions of the present invention also include a filler, preferably a mixture of hydrophobic fillers. A wide variety of inorganic, hydrophobic fillers may be employed such as silicas, aluminas, magnesias, titanias, inorganic salts, metallic oxides and glasses. It is preferred, however, that forms of silicone be employed, In accordance with the present invention, it has been found to be preferable to employ mixtures of silicas, including those derived form: crystalline silicone dioxide, such as: pulverized quartz; amorphous silicone dioxides, such as a diatomaceous earth (4–7$\mu$); and calcium sulfate. The sizes and surface areas of the foregoing materials are controlled to control the viscosity and thixotropicity of the resulting compositions,. Some or all of the foregoing hydrophobic fillers may be superficially treated with one or more silanating or "keying" agents, as known to those of ordinary skill in the art. Such silanating may be accomplished through use of known halogenated silanes or silazides. The fillers are present, preferably, in amounts of from about 35 to about 55 weight percent of the composition, forming an impression composition that is a putty. The fillers, more preferably, are about 40–50 weight percent of the composition. A preferred filler mixture includes 19–30 weight percent crystalline silicone dioxide, 15–25 weight percent amorphous silicone dioxide and 4–6 weight percent of calcium sulfate. A most preferred filler is about 24% cristobalite at about 7–28$\mu$ particle diameter, about 20% diatomaceous earth at about 4–7$\mu$ particle diameter and about 5% calcium sulfate.

A chemical system may be employed to diminish the presence or- degree of hydrogen outgassing which may be typically generated as a result of the vinyl polymerization. The composition thus may comprise a finely divided platinum metal that scavenges for and takes up such hydrogen. The Pt metal may be deposited upon a substantially insoluble salt having a surface area of between about 0.1 and 40 m$^2$/g. Suitable salts are barium sulphate, barium carbonate and calcium carbonate of suitable particle sizes. Other substrates include diatomaceous earth, activated alumna, activated carbon and others. The inorganic salts are especially preferred to lend improved stability to the resulting materials incorporating them. Dispersed upon the salts is about 0.2 to 2 parts per million of platinum metal, based upon the weight of the catalyst component. It has been found that employment of the platinum metal dispersed upon inorganic salt particles substantially eliminates or diminishes hydrogen outgassing during curing of dental silicones.

An important improvement of the invention is inclusion in the composition of a surfactant that imparts wettability and emulsion of the composition, as indicated by a surface contact angle with water at three minutes of less than 50°. An unexpected result of the selection of surfactant provides a major clinical advantage in that the wetting contact angle of less than 50° is achieved in less than about two minutes, decreasing and remaining below 50 throughout the working time of the composition, in contrast with prior art polyvinylsiloxanes and surfactant formulations that require more time to wet out. This higher wetting rate of the composition of the invention is particularly advantageous during the impression taking process and is shown in the Drawings.

Figure 1:
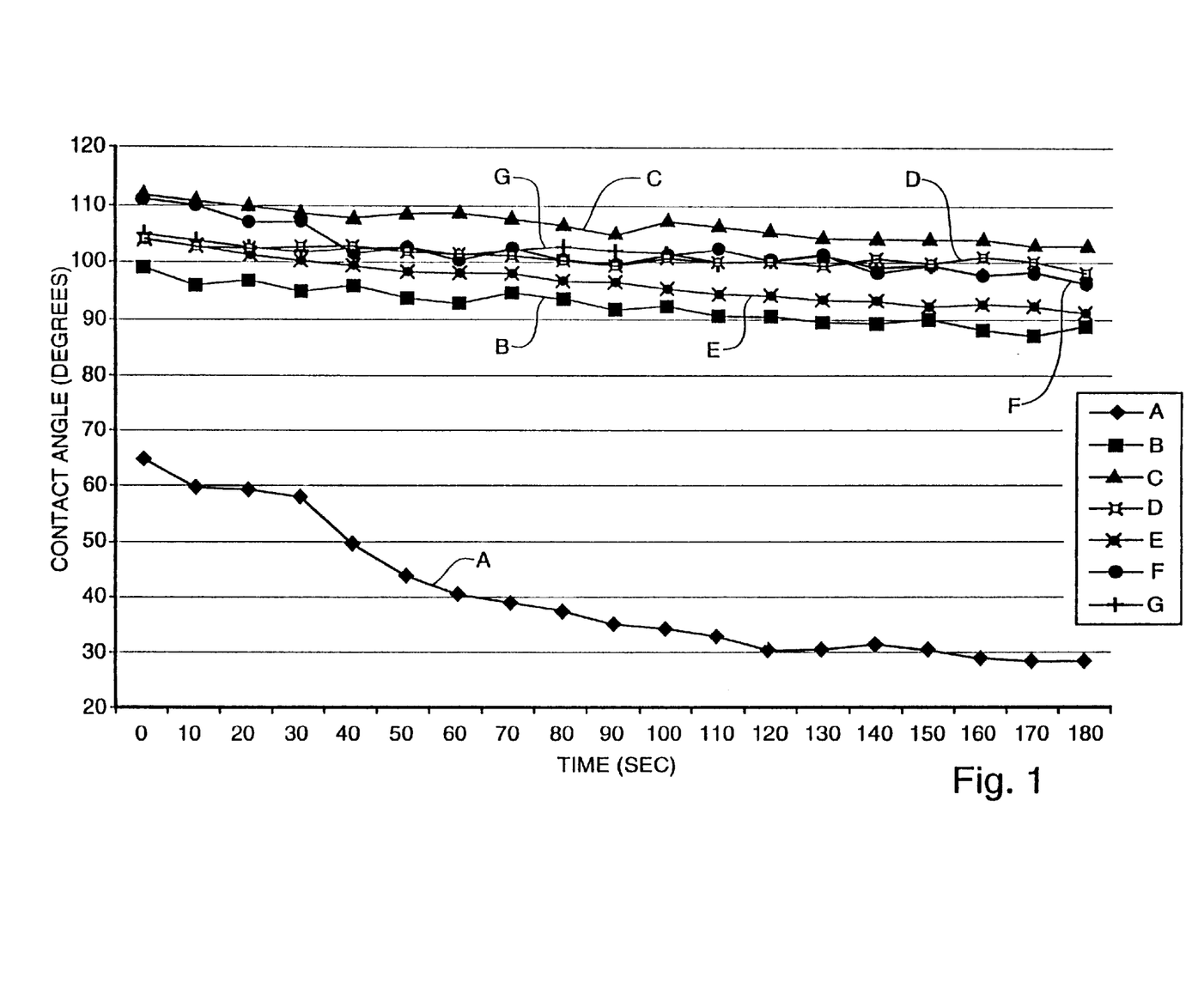
FIG. 1 is a graph showing wetting contact angle in degrees as a function of time in seconds.

Referring to FIG. 1, the Wetting Contact Angle, in degrees, as a function of Time, in minutes, is shown for the polyvinyl siloxane composition of the invention, in comparison with prior art compositions. Curve A shows that the composition of the invention has a wetting contact angle of about 50° at two minutes after mixing of the base and catalyst components. FIG. 1 shows that higher wettability is achieved early and improves at a fast rate over the about 2.5 minutes of useful working life of the impression taking material. Curves B through G show that the materials are hydrophobic with poor wetting, conventional polyvinyl siloxane impression materials of the prior art.

TABLE 1

| TIME (SEC) | EXAMPLE 1 (A) | REPROSIL (B) | WATER MARK (C) | PRESIDENT (D) | EXAFLEX (E) | EXTRUDE XT (F) | EXPRESS (G) |
|---|---|---|---|---|---|---|---|
| 0 | 65 | 99 | 112 | 104 | 104 | 111 | 105 |
| 10 | 60 | 96 | 111 | 103 | 103 | 110 | 104 |
| 20 | 59 | 97 | 110 | 103 | 102 | 107 | 103 |
| 30 | 58 | 95 | 109 | 103 | 101 | 107 | 102 |
| 40 | 50 | 96 | 108 | 103 | 100 | 102 | 103 |
| 50 | 44 | 94 | 109 | 102 | 99 | 103 | 103 |
| 60 | 41 | 93 | 109 | 102 | 99 | 101 | 101 |
| 70 | 40 | 95 | 108 | 102 | 99 | 103 | 102 |
| 80 | 38 | 94 | 107 | 101 | 97 | 101 | 104 |
| 90 | 36 | 92 | 105 | 102 | 97 | 100 | 103 |
| 100 | 35 | 93 | 108 | 101 | 96 | 102 | 103 |
| 110 | 34 | 91 | 107 | 101 | 95 | 103 | 100 |
| 120 | 31 | 91 | 106 | 101 | 95 | 101 | 101 |
| 130 | 32 | 90 | 105 | 100 | 94 | 103 | 102 |
| 140 | 33 | 90 | 105 | 102 | 94 | 99 | 100 |
| 150 | 32 | 91 | 105 | 101 | 93 | 100 | 101 |
| 160 | 30 | 89 | 105 | 102 | 94 | 99 | 98 |
| 170 | 30 | 88 | 104 | 101 | 93 | 99 | 100 |
| 180 | 30 | 90 | 104 | 99 | 92 | 98 | 97 |

TABLE 1A

| PROPERTY TESTED | EXAMPLE 1 (A) | REPROSIL (B) | WATER MARK (C) | PRESIDENT (D) |
|---|---|---|---|---|
| WORK TIME ['(minutes) "(seconds)] | 2'30" | 3'30" | 3'30" | 2'30" |
| SET TIME ['(minutes) "(seconds)] | 3'20" | 6'20" | 6'00" | 5'10" |
| % COMPRESSION SET | 0.45 | 0.30 | 0.35 | 0.30 |
| % STRAIN IN COMPRESSION | 1.40 | 1.40 | 2.70 | 1.50 |
| CONTACT ANGLE AT 2 MINUTES | 31 | 91 | 106 | 101 |
| DETAIL REPRODUCTION (MICRON) | 20 | 20 | 20 | 20 |
| SHORE A HARDNESS | 64 | 46 | 48 | 56 |
| TEAR STRENGTH (psi) | 364 | 188 | 298 | 295 |
| MIX CONSISTENCY (mm) | 22 | 24 | 21.4 | 27.0 |

TABLE 1B

| PROPERTY TESTED | EXAFLEX (E) | EXTRUDE XT (F) | EXPRESS (G) |
|---|---|---|---|
| WORK TIME | 1'55" | 3'00" | 3'00" |
| SET TIME | 4'20" | 6'30" | 6'15" |
| % COMPRESSION SET | 2.10 | 0.35 | 0.40 |
| % STRAIN IN COMPRESSION | 1.20 | 2.00 | 1.20 |
| CONTACT ANGLE AT 2 MINUTES | 95 | 101 | 101 |
| DETAIL REPRODUCTION | 20 MICRON | 20 MICRON | FAILED |
| SHORE A HARDNESS | 73 | 51 | 51 |
| TEAR STRENGTH (psi) | 384 | 244 | 168 |
| MIX CONSISTENCY (mm) | 29 | 29.0 | 27 |

Table 1, 1A and 1B show the composition of the Example 1 as A in comparison to prior a,: composition designated as B (REPROSIL), C (WATER MARK), D (PRESIDENT), E (EXAFLEX), F (EXTRUDE XP), G (EXPRESS). REPROSIL (B) is a dental impression material manufactured and sold by DENTSPLY International Inc. WATER MARK (C) is a dental impression material manufactured and sold by Generic/Pentron. PRESIDENT (D) is a dental impression material manufactured and sold by Coltene. EXAFLEX (E) is a dental impression material manufactured and sold by GC Dental. EXTRUDE XT (F) is a dental impression material manufactured and sold by Carr. Manufacturing. EXPRESS (G) is a dental impression material manufactured and sold by 3M.

Figure 2:
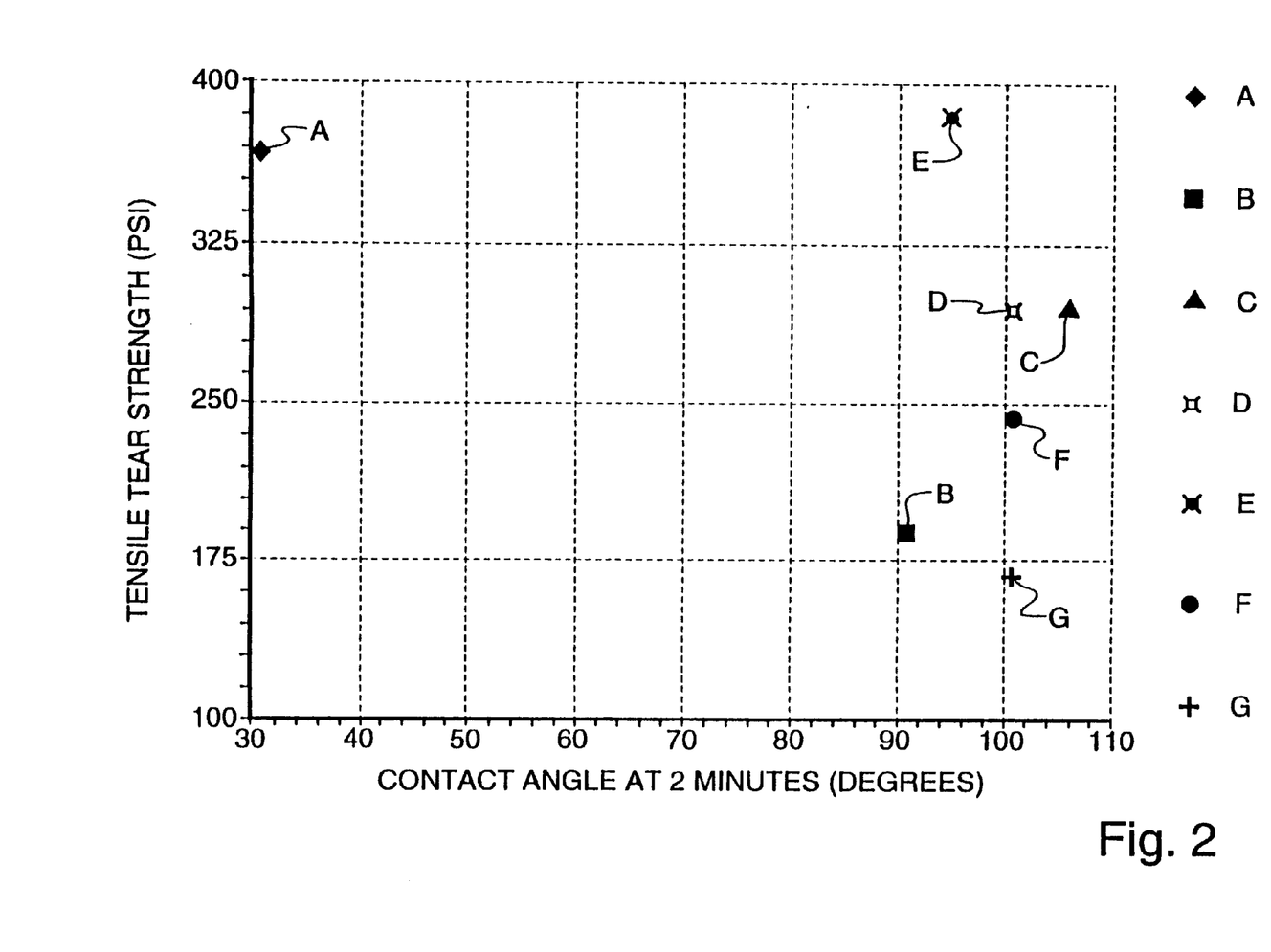
FIG. 2 is a graph showing tear strength in PSI as a function of contact angle in degrees. Contact angle measured at 2 minutes.

FIG. 2 shows impression material tear strength as a function of contact angle for the composition of the invention as compared to prior art. This in comparison to FIG. 1 shows the improved wettability and tear strength of the invention over putties of prior art. Tables 1A and 1B show the physical properties of the composition of the invention of Example 1 (A) compared to prior art materials (B–G).

The surfactant of the invention may be of cationic, anionic, amphoteric or nonionic type. A key criteria for selection is that the Hydrophobic Liphophilic Balance (HLB) value (described by Gower, "Handbook of Industrial Surfactants", 1993) must be in the range of 8–11. As is well-known, the higher the RIB the more hydrophobic is the substance. In addition, the, pH of the surfactant must be in the 6–8, range to prevent side reactions that may be detrimental the polymerization of the impression. A preferred surfactant is nonionic, having an HLB value of 10.8 comprising nonylphenoxypoly(ethyleneoxy) ethanol, sold by Rhone-Poulenc of Cranbury, N.J. as Igepal CO-530. In comparison it is noted above with respect to Bryan et al, in U.S. '1959 that Igepal CO-630, having an HLB of 13.0, differing in structure from CO-530 wherein the number of repeating units in CO-630 is 9 and those of CO-530 is 6, is not effective, demonstrating the criticality of the HLB limitation.

The composition of the invention includes plasticizers that beneficially alter the handling properties of the impression material. A preferred emulsifying plasticizer is octyl benzyl phthalate. Other phthalates are useful.

The composition of the invention may include various pigments to achieve a preferred color. Such pigments are well known and include titanium dioxide and iron oxides as well as many others.

The two component compositions prepared in accordance with the instant invention are employed in the same way that conventional impression materials have been employed. Thus, appropriately equal portions of base paste and catalyst paste are mixed together thoroughly and applied to the oral dentition or other region for a period of time sufficient for the polymerizations or hardening of the composition. Once the composition has been substantially hardened, it is removed from the mouth or other surface and used for the elaboration of casts and the like from which representations of the casting surface are subsequently prepared.

As will be appreciated by those of ordinary skill in the art, it is important that dental silicone materials be, capable of being stored for reasonably long periods of time and at reasonable storage temperature in order to maximize their commercial utility. Accordingly, it is necessary that such materials not suffer from decreased physical properties or substantial changes in working time or hardening time upon such storage. In this regard, accelerated storage tests employing high ambient temperatures are now capable of determining the shelf stability of such materials.

Certain embodiments of the present invention are described below. Numerous other compositions and formulations may be prepared within the spirit of the invention. The following examples are not to be construed as limiting and are offered by way of illustration.

EXAMPLE 1

The two component composition of the invention is formulated in a Base Paste and Catalyst Paste components. Mixing of each component's ingredients, is done in a double planetary mixer having a mixing pot heated with circulating water at 40° C.–50° C. and under 65 mm mercury vacuum.

Base Paste Component

In making the Base Paste, the mixing pot is first charged with all organohydrogen polysiloxane and incrementally thereafter, with GM dispersion, linear polysiloxane, plasticizer surfactant and filler component, with mixing continuing until a uniform mixture is achieved. The finished Base Paste is discharged into a storage container.

Catalyst Paste Component

The Catalyst Paste component is formulated and mixed under conditions and in equipment as described above. The platinum catalyst, 1,3 divinyldimethyldisiloxane, QM resin dispersions, linear PVS, plasticizer fillers and pigments are added incrementally to the mixing pot and mixing carried out until a uniformly mixed mass is achieved. The compounded Catalyst Paste is then discharged into a storage container The composition of each component is indicated in the table below, wherein amounts are in weight percent of the component.

|  | BASE | CATALYST |
|---|---|---|
| Organohydrogen Polysiloxane (Very high viscosity (PVS) | 5.00 | 0.00 |
| (5,000–7,000 mpa's) QM Resin Dispersion | 0.00 | 0.00 |
| (45000–60000 mpa's) QM Resin Dispersion | 28.50 | 33.10 |
| (165.000 mpa's) Divinyl Polysiloxane | 0.00 | 0.00 |
| (400,000–500,1000 Mw) Divinyl Polysiloxane | 10.00 | 10.00 |
| Cristobalite | 24.35 | 14.00 |
| Diatomaceious earth | 20.00 | 5.00 |
| Silanated Fumed Silica | 0.00 | 0.00 |
| Dried Calcium Sulfate | 5.00 | 5.00 |
| Titanium Oxide Pigment (Iron Oxide) | 0.15 | 0.00 |
| Surfactant (Igepal CO-530) | 2.50 | 0.00 |
| Plasticizer | 4.50 | 4.50 |
| Platinum Catalyst | 0.00 | 0.75 |
| 1,3-Divinyldimethyidisiloxane | 0.00 | 0.10 |
| Finely divided Platinum metal | 0.00 | 0.20 |
| on Calcium Carbonate | | |
| | 100.00 | 100.00 |

EXAMPLE 2

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane (Very high viscosity (PVS) | 6.00 | 0.00 |
| (5,000–7,000 mpa's) QM Resin Dispersion | 22.16 | 22.56 |
| (45000–60000 mpa's) QM Resin Dispersion | 0.00 | 0.00 |
| (165.000 mpa's) Divinyl Polysiloxane | 22.16 | 26.56 |
| (400,000–500,1000 Mw) Divinyl Polysiloxane | 0.00 | 0.00 |
| Cristobalite | 0.00 | 0.00 |
| Diatomaceious earth | 29.53 | 29.54 |
| Silanated Fumed Silica | 1.00 | 1.00 |
| Dried Calcium Sulfate | 5.00 | 5.00 |
| Titanium Oxide Pigment (Iron Oxide) | 0.15 | 0.00 |
| Surfactant (Igepal CO-530) | 8.00 | 0.00 |
| Plasticizer | 6.00 | 10.00 |
| Platinum Catalyst | 0.00 | 0.80 |
| 1,3-Divinyldimethyidisiloxane | 0.00 | 0.04 |
| Finely divided Platinum metal | 0.00 | 0.50 |
| on Calcium Carbonate | | |
| | 100.00 | 100.00 |

EXAMPLE 3

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane (Very high viscosity (PVS) | 6.00 | 0.00 |
| (5,000–7,000 mpa's) QM Resin Dispersion | 0.00 | 0.00 |
| (45000–60000 mpa's) QM Resin Dispersion | 22.16 | 26.56 |

-continued

|  | BASE | CATALYST |
|---|---|---|
| (165.000 mpa's) Divinyl Polysiloxane | 22.16 | 26.56 |
| (400,000-500,1000 Mw) Divinyl Polysiloxane | 0.00 | 0.00 |
| Cristobalite | 0.00 | 0.00 |
| Diatomaceious earth | 29.53 | 29.74 |
| Silanated Fumed Silica | 1.00 | 1.00 |
| Dried Calcium Sulfate | 5.00 | 5.00 |
| Titanium Oxide Pigment (Iron Oxide) | 0.15 | 0.00 |
| Surfactant (Igepal CO-530) | 8.00 | 0.00 |
| Plasticizer | 6.00 | 10.00 |
| Platinum Catalyst | 0.00 | 0.60 |
| 1,3-Divinyldimethyidisiloxane | 0.00 | 0.04 |
| Finely divided Platinum metal | 0.00 | 0.50 |
| on Calcium Carbonate |  |  |
|  | 100.00 | 100.00 |

EXAMPLE 4

A two component composition of the invention is made by first making a Base Paste and then a Catalyst Paste, as described in Example 1, having the composition indicated in the table below.

|  | BASE | CATALYST |
|---|---|---|
| Organohydrogen Polysiloxane (Very high viscosity (PVS) | 5.00 | 0.00 |
| (5,000–7,000 mpa's) QM Resin Dispersion | 0.00 | 0.00 |
| (45000–60000 mpa's) QM Resin Dispersion | 17.54 | 21.35 |
| (165.000 mpa's) Divinyl Polysiloxane | 27.31 | 32.03 |
| (400,000 . 500,1000 Mw) Divinyl Polysiloxane | 0.00 | 0.00 |
| Cristobalite | 0.00 | 0.00 |
| Diatomaceious earth | 33.50 | 32.05 |
| Silanated Fumed Silica | 1.00 | 1.00 |
| Dried Calcium Sulfate | 5.00 | 5.00 |
| Titanium Oxide Pigment (Iron Oxide) | 0.15 | 0.00 |
| Surfactant (Igepal CO-530) | 6.00 | 0.00 |
| Plasticizer | 4.50 | 7.50 |
| Platinum Catalyst | 0.00 | 0.25 |
| 1,3-Divinyldimethyidisiloxane | 0.00 | 0.03 |
| Finely divided Platinum metal | 0.00 | 0.80 |
| on Calcium Carbonate |  |  |
|  | 100.00 | 100.00 |

EXAMPLE 5

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane (Very high viscosity (PVS) | 6.00 | 0.00 |
| (5,000–7,000 mpa's) QM Resin Dispersion | 0.00 | 0.00 |
| (45000–60000 mpa's) QM Resin Dispersion | 27.80 | 33.57 |
| (165.000 mpa's) Divinyl Polysiloxane | 0.00 | 0.00 |
| (400,000–500,1000 Mw) Divinyl Polysiloxane | 0.00 | 0.00 |
| Cristobalite | 40.05 | 41.70 |
| Diatomaceious earth | 15.00 | 13.50 |
| Silanated Fumed Silica | 0.00 | 0.00 |
| Dried Calcium Sulfate | 5.00 | 5.00 |
| Titanium Oxide Pigment (Iron Oxide) | 0.15 | 0.00 |
| Surfactant (Igepal CO-530) | 2.50 | 0.00 |

-continued

|  | BASE | CATALYST |
|---|---|---|
| Plasticizer | 3.50 | 5.00 |
| Platinum Catalyst | 0.00 | 0.40 |
| 1,3-Divinyldimethyidisiloxane | 0.00 | 0.03 |
| Finely divided Platinum metal | 0.00 | 0.80 |
| on Calcium Carbonate |  |  |
|  | 100.00 | 100.00 |

EXAMPLE 6

A representative sample of each of the above described Examples, of 10 grams, is mixed in equal parts and the properties of the mixture and resulting polymerized composition tested. Table 2 below reports the results said measurements. The first five properties reported (work time, set time, compression set, strain in compression and tear strength) are tested in accord with ADA Specification 19: Non-Aqueous Elastomer Impression Materials (1976, as amended in 19a of 1982) incorporated herein by reference.

The following procedure was used to provide tensile tear strength, percent elongation, and modulus of elasticity of the Examples.

Equal parts of the base and catalyst components are mixed and the samples or specimen is placed in a specimen mold having an I-shaped cavity that is 1.5 mm thick, 20 mm×11 mm, with top arms of 8 mm depth and center I portion 5 mm wide. The filled mold is clamped between two stainless steel plates and the assembly is placed in a 32° C. water bath. At six minutes from start of mix, the assembly is removed from the bath. The mold is unclamped, the specimen is removed from the mold and any flash is removed from the specimen. At 10 minutes from start of mix the specimen is clamped into the specimen test grips of an Instron Model 1123-R in the extension mode. The Instron is attached to a computer with Instron's Series 9 software that has been programmed to calculate the tear strength [psi], % elongation, and modulus of elasticity. At 11 minutes, the specimen is stressed by the Instron at a rate of 10 mm/min. until the specimen reaches peak failure. (The maximum load is set to 5 kg.) This is repeated for five specimens and then statistically evaluated results are reported, as shown in the Table 2.

Wetting contact angles are measured for each Example as follows. One gram (1g) of base and one gram (1g) of catalyst paste are mixed together until uniform (~30 seconds). A one-half gram (0.5 g) of mixed paste is placed between two sheets of polyethylene (Dentsilk) and pressed flat using a glass plate, about 2–3 mm thick. The specimen is allowed to stand undisturbed until set (~15 minutes). The polyethylene sheets are removed, being careful not to touch the surface of the specimen, and the specimen placed on the table of a gynometer, a well known device for measuring contact angles. The contact angle was then measured from 0 to 3 min using AST Products VCA 2500 XE Video contact angle system.

Putty composition in accordance with the invention preferably have a tear strength of at least 250 psi. More preferably, putty compositions in accordance with the invention have a tear strength of at least 300 psi.

TABLE 2

| PHYSICAL PROPERTIES | EXAMPLE 1 | EXAMPLE 2 | EXAMPLE 3 | EXAMPLE 4 | EXAMPLE 5 |
|---|---|---|---|---|---|
| WORK TIME | 2;'00" | 1'05" | 2'00" | 2'00" | 2'20" |
| SET TIME | 4'30" | 2'10" | 4'00" | 4'10" | 3'40" |
| % COMPRESSION SET | 0.5 | 0.5 | 0.45 | 0.5 | 0.4 |
| % STRAIN IN COMPRESSION | 1.5 | 2 | 2.5 | 2. | 1.8 |
| TEAR STRENGTH (psi) | 328 | 115 | 142 | 178 | 155 |
| % ELONGATION | 41 | 79 | 77 | 73 | 61 |
| CONTACT ANGLE AT 2 MINUTES | 32 | 39 | 36 | 43 | 42 |
| DETAIL REPRODUCTION (MICRONS) | 20 | 20 | 20 | 20 | 75 |
| HANDLING PROPERTY | GOOD, NONSTICKY | STICKY | GOOD, NONSTICKY | GOOD, NONSTICKY | GOOD, NONSTICKY |
| STABILITY | NO SEPARATION | SEPARATION | SEPARATION | SEPARATION | SEPARATION |

The preferred composition of Example 1 is very suitable for hand mixing providing a soft easy mix that is non-sticky to the bare or gloved hard. Example (1) is hydrophilic and produces highly detailed impressions of moist oral tissue. The composition of Example (1) gives the cured impression improved tear strength for more accurate impressions. The composition of example (1) has improved shelf life with no separation of liquid and solid phases.

The composition of Examples 2–5 are useful as putty impression materials but have the following deficiencies. Example 2 produced a composition that provided a hydrophilic impression but was low in tear strengths sticky to the hands, and has severe separation of the liquid and solid phases during shelf life testing. The procedures of Examples 3 and 4 each produce a composition that is hydrophilic and useful for dental impressions and has good handling but each is low in tear strength and has moderate separation of the liquid and solid phases during shelf life testing. Example (5) produced a composition that provided hydrophilic impressions and good handling but is low in tear strength and has slight separation of the liquid and solid phases during shelf life testing.

EXAMPLE 7

A liquid is prepared by mixing 2.5 grams of polymethylhydrogensiloxane (CAS No. 68037-59-2), 30.025 grams of siloxane vinyl Q-resin dispersion (CAS No.. 68083–19–2), 10 grams of vinyl-terminated polydimethylmethylvinylsiloxane (CAS No. 68083-18-1), 0.7350 grams of divinyl polydimethylsiloxane (CAS No. 68038-19-2), 1.25 grams of nonlyphenol-ethoxalated (CAS No. 9016-45-9), 4.5 grams of octyl benzyl phthalate (CAS No. 68515-40-2), 0.015 grams of organoplatinum complex, and 0.05 grams of 1,3 divinyltetramethyldisiloxane (CAS No. 2627-95-4). Filler is prepared by mixing 29.05 grams of surface treated silicon dioxide (CAS No. 100402-83), 16 grams of silicone dioxide, amorphous (CAS No. 7631-86-9), 5 grams of calcium sulfate (CAS No. 10101-41-4), 0.008 grams of platinum (CAS No. 471-34-1), 0.152 grams of calcium carbonate (CAS No. 7440-06-4), and 0.64 grams of silicone dioxide, crystalline (CAS No. 14464-46-1). The liquids and fillers are mixed by hand to form a putty. The putty is placed in a tray and inserted into a patient's mouth. The, patient bites the putty material opening his mouth to leave a dental impression in the material. Alternatively, the dentist inserts the putty in a tray and presses it against the patient's dentition. The dental impression is filled with plaster to form a plaster cast of the patient's teeth.

EXAMPLE 8

A base liquid is formed by mixing 5 grams of polymethylhydrogensiloxane (CAS No. 68037-59-2), 26.5 grams of siloxane vinyl Q-resin dispersion (CAS No. 68083-19-2), 10 grams of vinyl-terminated polydimethylmethylvinylsiloxane (CAS No. 68083-18-1), 2.5 grams of nonylphenol-ethoxalated (CAS No. 9016-45-9), and 4.5 grams of octyl benzyl phthalate (CAS No. 68515-40-2). A catalyst liquid is formed by mixing 32.9 grams of siloxane vinyl Q-resin dispersion (CAS No. 68083-19-2), 10 grams of vinyl-terminated polydimethylmethylvinylsiloxane (CAS No. 68083-18-1),0.735 grams of divinylpolydimethylsiloxane (CAS No. 68083-19-2), 4.5 grams of octyl benzyl phthalate (CAS No. 68515-40-2), 0.015 grams of organoplatinum complex, and 0.1 grams of 1,3 divinyltetramethyldisiloxane (CAS No. 2627-95-4). Base pigmented filler is formed by mixing 24.35 grams of surface treated silicone dioxide (CAS No. 100402-83), 20 grams of silicone dioxide, amorphous (CAS No. 7631-86-9), and 5 grams of calcium sulfate (CAS No. 10101-41-4). Catalyst pigmented filler is prepared by mixing 31.8 grams of surface treated silicone dioxide (CAS No. 100402-83), 14 grams of silicone dioxide, amorphous (CAS No. 7631-86-9), 5 grams of calcium sulfate (CAS No. 10101-41-4), 0.008 grams of platinum (CAS No. 471-34-1), 0.152 grams of calcium carbonate (CAS No. 7440-06-4), 0.640 grams of silicone dioxide, crystalline (CAS No. 14464-46-1) A base liquid and base pigmented filler is mixed to form a base putty. A catalyst liquid is mixed with pigmented catalyst filler in a one to one ratio by weight for form a catalyst putty. In use, a one to one ratio by weight of base putty and catalyst putty are mixed to form putty impression material.

The physical properties of the dental impression material formed in Example 8 are as follows in Table 3:

TABLE 3

| PROPERTY | AQUASIL PUTTY |
|---|---|
| Work Time (Min.) | 2'00" |
| Set Time (Min.) | 4'00" |
| Permanent Deformation (%) | 0.35 |
| Linear Dimensional Chance (%) | −1.13 |
| Detail Reproduction/Compability with Gypsum (Microns) | 20 |
| Mix Consistency (mm) | 24 |
| Strain In Compression (%) | 1.4 |
| Tear Strength (PSi) | 364 |
| Water Contact Angle at 3 Minutes (Degrees) | 33 |

The putty formed in Examples 7 and 8 are hydrophilic, have high tear strength and are easily mixed. Beneficially the impression material formed in Examples 7 and 8 retain octyl benzyl phthalate which does not form droplets on the surface thereof. This is a superior result over many prior art dental impression materials. Furthermore, the dental impression material formed in Example 7 and formed in Example 8 is non-tacky, which makes it readily mixable in the hands of the user. The dental impression materials of Examples 7 and 8 are stable and the components thereof do not separate within one week at 23° C.

The plasticizer is used to reduce tackiness of the composition during mixing of the base and catalyst components which are preferably mixed by hand kneading. Preferably the plasticizer comprised an alkylphthalate at about 4–5% by weight of the base and catalyst compositions. Most preferably, the alkyl phthalate is octyl benzyl phthalate.

An embodiment of the invention provides a two component hydrophilic polymerizable polyorganosiloxane separation stable composition for making a low liquid mass loss non-sweating dental impression having a consistency of less than 32 mm, one component including a catalyst for polymerization, the composition, including:

(a) a QM resin, containing vinyl groups;

(b) a linear vinyl terminated polydimethyl-siloxane fluid, forming with the QM resin a dispersion having a vinyl content of about 0.16 to 0.24 m-mole/g;

(c) a linear vinyl terminated polydimethylsiloxane having a gram molecular weight of at least 400,000 to 500,000 including 5–15 percent by weight of the composition.

(d) an organohydrogen polysiloxane for cross-linking the vinyl groups;

(e) an organoplatinum catalyst complex for accelerating polymerization of the components;

(f) an emulsifying plasticizer;

(g) a retarder component in sufficient amount for temporarily delaying the onset of the polymerization;

(h) a filler; and (i) a surfactant that imparts wettability to the composition, wherein the composition surface contact angle with water is less than 50° after three minutes wherein the QM resin-containing dispersion comprise: a dispersion having a viscosity of about 45,000–60,000 cps, the QM resin including about 20–25 weight % of the dispersions.

Preferably the dispersion of (a) and (b) has a viscosity of about 45,000–60,000 cps.

Preferably the QM resin comprises a polyorganosiloxane including units of $SiO_2$ and up to four units of $R^1R^2$, $SiO_{1/2}$ wherein $R^1$ is unsaturated hydrocarbon and $R^2$ is aklyl or aryl.

Preferably the QM resin comprises the formula:

Preferably the composition includes a finely divided platinum metal, sufficient to scavenge excess hydrogen gas generated during polymerization of the composition. Preferably the retarder component is a low molecular weight, vinyl functional fluid that is a linear or cyclic polysiloxane, in an amount of at least about 0.030 weight percent of the composition. Preferably the retarder component comprises: a fluid 1,3-divinyl, dimethyldisiloxane, in an amount of about 0.05 to 0.15 weight percent of the composition. Preferably the emulsifying plasticizer is capable of being emulsified to prevent sweating and migrating to the surface of placticizer from the polymerized impression. Preferably the plasticizer is octyl benzyl phthalate. Preferably the filler comprises about 40 to about 90 weight percent of the composition. Preferably the filler comprises a mixture of about 19–30 weight percent crystalline silicone dioxide, about 15–25 weight percent amorphous silicone dioxide and about 4–6 weight percent calcium sulfate each based on 100% weight percent of the composition. Preferably the surfactant comprises an HLB of about 8–11 and a pH of about 6–8. Preferably the surfactant is a nonionic surfactant. Preferably the surfactant is a nonylphenoxypoly (ethylenoxy)ethanol having an HLB of about 10.8. Preferably the composition after polymerization, through chemical bonding, has a tear strength of about 300–400 psi (2.07 to 2.76 MPa) and a contact angle with water of less than 50° at three minutes.

An embodiment of the invention provides a method to making a dental impression, in a wet environment, of oral hard and soft tissues, including:

mixing a two component hydrophilic non-sweating polymerizable polyorganosiloxane separation stable composition, including a polymerizable catalyst including, (a) a QM resin, containing vinyl groups, (b) a linear vinyl terminated polydimethyl-siloxane fluid, forming with the QM resin a dispersion having a viscosity of about 45000–65,000 cps and a vinyl content of about 0.16 to 0.24 m-mole/g, (c) a viscosity linear vinyl terminated polydimethylsiloxane having a gram molecular weight of at least 400,000 to 500,000 including 5–15 percent by weight of the composition.

(d) an organohydrogen polysiloxane for cross-linking the vinyl groups;

(e) an organoplatinum catalyst complex for accelerating polymerization of the components;

(f) an emulsifying plasticizer;

(g) a retarder component in sufficient amount for temporarily delaying the onset of the polymerization;

(h) a filler; and (i) a surfactant that imparts wettability to the composition, wherein the composition surface contact angle with water is less than 50° after three minutes wherein the QM resin-containing dispersion comprise: a dispersion having a viscosity of about 45,000–60,000 cps, the QM resin including about 20–25 weight % of the dispersions, placing the mixture into contact with the tissues;

allowing the mixture to harden into the impression; and removing the impression from the tissues;

wherein the QM resin-containing dispersion, includes a dispersion having a viscosity of about 45,000–60,000 cps, the QM resin including about 20–25 weight % of the dispersions.

Preferably the composition surface contact angle with water is less than about 50° from about two minutes from placing until the impression hardens. Preferably the dental impression is a low liquid mass loss elastomeric material. Preferably the dental impression has a tear strength of at least about 300 psi and a surface contact angle with water at three minutes of less than about 50°.

An embodiment of the invention provides a dental impression putty material formed by the process of:

providing a two component hydrophilic non-sweating polymerizable polyorganosiloxane separation stable composition having a consistency of less than 32 mm, one component including a catalyst for polymerization, the composition, including:

(a) a QM resin, containing vinyl groups;

(b) a linear vinyl terminated polydimethyl-siloxane fluid, forming with the QM resin a dispersion having a vinyl content of about 0.16 to 0.24 m-mole/g;

(c) a linear vinyl terminated polydimethylsiloxane having a gram molecular weight of at least 400,000 to 500,000 including 5–15 percent by weight of the composition.

(d) an organohydrogen polysiloxane for cross-linking the vinyl groups;

(e) an organoplatinum catalyst complex for accelerating polymerization of the components;

(f) an emulsifying plasticizer;

(g) a retarder component in sufficient amount for temporarily delaying the onset of the polymerization;

(h) a filler; and (i) a surfactant that imparts wettability to the composition, wherein the composition surface contact angle with water is less than 50° after three minutes wherein the QM resin-containing dispersion comprise: a dispersion having a viscosity of about 45,000–60,000 cps, the QM resin including about 20–25 weight % of the dispersions.

It should be understood that while the present invention has been described in considerable detail with respect to certain specific embodiments thereof, it should not be considered limited to such embodiments but may be used in other ways without departure from the spirit of the invention and the scope of the appended claims.

A preferred embodiment of the invention provides a very high viscosity putty polyvinylsiloxane impression material useful to record hard and soft tissues in the mouth. The impression material is a two component, hydrophilic non-sweating polymerizable organosiloxane separation stable material. The two component polymerizable organosiloxane composition, preferably has one component which includes a catalyst for polymerization. The composition is for making a dental impression and comprises:

(a) a QM resin, containing vinyl groups;

(b) a linear vinyl terminated polydimethyl-siloxane fluid, forming with the QM resin a dispersion having a vinyl content of about 0.16 to 0.24 m-mole/g;

(c) a very high viscosity linear vinyl terminated polydimethylsiloxane having a molecular weight of 400,000–500,000, vinyl content 0.03 mmole/g;

(d) an organohydrogen polysiloxane for cross-linking the vinyl groups;

(e) an organoplatinum catalyst complex for accelerating polymerization of the components;

(f) an emulsifying plasticizer; Plasticizer is normally an oily liquid. Plasticizer typically is a low molecular weight nonpolymerizable compound, for example having a gram molecular weight less than 2000 and a viscosity less than 200 CPS.

(g) a retarder component in sufficient amount for temporarily delaying the onset of the polymerization;

(h) a filler; and

(i) a surfactant that imparts wettability to the composition, wherein the composition surface contact angle with water is less than 50° after three minutes.

In accordance with a preferred embodiment of the invention, the plasticizer is emulsified by the surfactant. The mixture of plasticizer and surfactant form a homogeneous phase within the putty composition in accordance with the invention. Preferably, the dispersion of (a) and (b) has a viscosity of about 45,000–60,000cps. The dispersion of (a), (b) and (c) may comprise a plurality of dispersion components having desired viscosities and QM resin contents. Preferably the QM resin-containing dispersions comprise a dispersion component having a viscosity of about 45,000–60,000 cps, the QM resin comprising about 20–25 weight % of the dispersion. A preferred QM resin comprises a polyorganosiloxane comprising units of $SiO_{4/2}$ and units of $R^1R^2_2\ SiO_{1/2}$ wherein $R^1$ is unsaturated, preferably vinyl and $R^2$ is alkyl, aryl, etc., such as methyl, ethyl, phenyl, etc. More preferably, the QM resin comprises the formula:

The very high viscosity linear vinyl terminated polydimethylsiloxane which imparts longer shelf stability, higher tear strength, reduced tackiness and improved tactile handling properties is preferably 5–15 percent by weight and most preferably 9–11 percent by weight of the composition. The retarder component of the composition preferably is a low molecular weight, vinyl functional fluid that is a linear or cyclic polysiloxane in an amount of at least about 0.010 weight percent of the composition. Preferably, the retarder component comprises: a fluid 1,3-divinyl, dimethyldisiloxane, in an amount of about 0.05 to 0.15 weight percent of the composition. The composition preferably includes a plasticizer that is capable of being emulsified to prevent "sweating" or migrating to the surface of the polymerized impression. The plasticizer is used to reduce tackiness of the composition during mixing of the base and catalyst components which are mixed by hand kneading. Preferably the plasticizer is comprised of an alkylphthalate, preferably at about 4–5 percent by weight of the base and catalyst compositions. Most preferably, the alkylphthalate is octyl benzyl phthalate. The filler component comprises about 35 to about 55 weight percent of the composition and preferably includes a filler mixture of about 40 to about 50 weight percent. The surfactant is for imparting wettability, and preferably comprises an HLB of about 8–11 and a pH of about 6–8. A most preferred surfactant is a nonionic surfactant, nonylphenoxy poly(ethyleneoxy) ethanol having an HLB of about 10.8. This surfactant also serves to emulsify the plasticizer and prevents its separation and "sweating" from the compositions. After polymerization, the compositions of the invention preferably include a tear strength of 300–400 psi and a contact angle with water of less than 50° at three minutes.

What is claimed is:

1. A method of making a hydrophilic non-sweating polymerizable polyorganosiloxane separation stable dental impression material, comprising:

providing a hydrophilic non-sweating polymerizable polyorganosiloxane separation stable dental impression material, including a catalyst, a resin having vinyl groups, a plasticizer and a surfactant, said surfactant being effective to emulsify said plasticizer, said dental impression material having a surface contact angle with water less than 50° after three minutes.

2. The method of claim 1 further comprising pressing said composition.

3. The method of claim 1 further comprising polymerizing said resin to form a solid polymeric dental impression having a tear strength of about 300 to 400 psi.

4. A method of making an impression, comprising:

mixing two components of a hydrophilic non-sweating polymerizable polyorganosiloxane separation stable putty material, one component including a catalyst for polymerization, said putty material, comprising: a resin, containing vinyl groups, a plasticizer and a surfactant; said surfactant being effective to emulsify said plasticizer, applying a low viscosity material, applying said putty material over the low viscosity material, whereby the low viscosity material is forced into the minute details of the patient's oral tissues, hardening said putty material and said low viscosity material within about five minutes to form an impression of said patient's oral tissues, and removing said impression from said patient's oral tissues.

5. A process, comprising:

providing two components of a hydrophilic non-sweating polymerizable polyorganosiloxane separation stable composition, one component including a catalyst for polymerization, said composition, comprising: a resin having vinyl groups, a plasticizer and a surfactant, said surfactant being effective to emulsify said plasticizer, pressing said composition, and polymerizing said resin to form a dental impression of solid polymeric material.

6. A method of making an impression, comprising:

mixing two components of a hydrophilic non-sweating polymerizable polyorganosiloxane separation stable composition, one component including a catalyst for polymerization, said composition, comprising: a resin, containing vinyl groups, a plasticizer and a surfactant; said surfactant being effective to emulsify said plasticizer, said composition surface contact angle with water being less than 50° after three minutes, contacting said mixture with tissues for making an impression; hardening said mixture into polymeric material having said impression; and removing said impression from said tissues.

7. The method of claim 6 wherein said polymeric material has a tear strength of about 300 to 400 psi.

8. An impression material formed by the process of:

providing two components of a hydrophilic non-sweating polymerizable polyorganosiloxane separation stable paste composition, one component including a catalyst for polymerization, said composition, comprising: a resin having vinyl groups, a plasticizer and a surfactant, said surfactant being effective to emulsify said plasticizer, said composition surface contact angle with water being less than 50° after three minutes, mixing said components to form said hydrophilic non-sweating polymerizable polyorganosiloxane separation stable paste composition, pressing said composition.

9. The impression material formed by the process of claim 8 further comprising a retarder, said retarder being effective to delay the onset of polymerization of said composition.

10. A dental impression paste material formed by the process of:

providing two components of a hydrophilic non-sweating polymerizable polyorganosiloxane separation stable composition having a consistency of less than 32 mm, one component including a catalyst for polymerization, said composition, comprising: a resin, containing vinyl groups, a plasticizer and a surfactant; said surfactant being effective to emulsify said plasticizer, said composition surface contact angle with water being less than 50° after three minutes, mixing said components of said composition to form a polymerizable dental impression paste material.

11. The material of claim 10 further comprising polymerizing said polymerizable dental impression paste material to form a solid polymeric dental impression.

12. A dental impression material formed by the process of:

providing two components of a hydrophilic non-sweating polymerizable polyorganosiloxane separation stable composition having a consistency of less than 32 mm, one component including a catalyst for polymerization, said composition, comprising: a resin, containing vinyl groups, a plasticizer and a surfactant; said surfactant being effective to emulsify said plasticizer, said composition surface contact angle with water being less than 50° after three minutes, and hardening said resin to form a solid polymeric dental impression.

13. A method of making a dental impression, in a wet environment, of oral hard and soft tissues, comprising:

mixing two components of a hydrophilic non-sweating polymerizable polyorganosiloxane separation stable composition having a consistency of less than 32 mm, one component including a catalyst for polymerization, said composition, comprising: a resin, containing vinyl groups, a plasticizer and a surfactant; said surfactant being affective to emulsify said plasticizer, said composition surface contact angle with water being less than 50° after three minutes, contacting said mixture with said tissues;

hardening said mixture into polymeric material having said impression; and removing said impression from said tissues.

14. The method of claim 13 wherein said polymeric material has a tear strength of about 300 to 400 psi.

* * * * *